United States Patent
Kawamura et al.

(10) Patent No.: US 11,980,706 B2
(45) Date of Patent: May 14, 2024

(54) AIR TRAP CHAMBER AND EXTRACORPOREAL CIRCULATION CIRCUIT

(71) Applicant: NIKKISO CO., LTD., Tokyo (JP)

(72) Inventors: Shunsuke Kawamura, Makinohara (JP); Shunichi Koda, Makinohara (JP)

(73) Assignee: NIKKISO CO., LTD., Tokyo (JP)

( * ) Notice: Subject to any disclaimer, the term of this patent is extended or adjusted under 35 U.S.C. 154(b) by 700 days.

(21) Appl. No.: 17/050,606

(22) PCT Filed: Mar. 11, 2019

(86) PCT No.: PCT/JP2019/009666
§ 371 (c)(1),
(2) Date: Oct. 26, 2020

(87) PCT Pub. No.: WO2019/211944
PCT Pub. Date: Nov. 7, 2019

(65) Prior Publication Data
US 2021/0113758 A1    Apr. 22, 2021

(30) Foreign Application Priority Data

May 2, 2018    (JP) ................................ 2018-088656

(51) Int. Cl.
*A61M 1/36* (2006.01)
*A61M 1/38* (2006.01)
*B01D 19/00* (2006.01)

(52) U.S. Cl.
CPC ........ *A61M 1/3638* (2014.02); *A61M 1/3653* (2013.01); *A61M 1/38* (2013.01); *B01D 19/0042* (2013.01)

(58) Field of Classification Search
None
See application file for complete search history.

(56) References Cited

U.S. PATENT DOCUMENTS

| 4,664,682 A | * | 5/1987 | Monzen | ............. | A61M 1/3632 96/219 |
|---|---|---|---|---|---|
| 5,328,461 A | | 7/1994 | Utterberg | | |

(Continued)

FOREIGN PATENT DOCUMENTS

| DE | 2 043 795 B1 | 5/1972 |
|---|---|---|
| EP | 3 266 477 A1 | 1/2018 |

(Continued)

OTHER PUBLICATIONS

Oct. 18, 2022 Office Action issued in Chinese Patent Application No. 201980028242.2.

(Continued)

*Primary Examiner* — Gabriel E Gitman
(74) *Attorney, Agent, or Firm* — Oliff PLC (57) ABSTRACT

An air trap chamber is provided with a cap and a housing. The cap has an inlet port provided at one end, and has, at another end, a first connection flange provided so as to have an inner circumferential surface. An opening axis of the inlet port is set so as to be off a center axis of the inner peripheral surface. The housing has, at one end, a second connection flange provided so as to have an outer circumferential surface which is mated to the inner circumferential surface, and has an outlet port provided at another end. An opening axis of the outlet port is set so as to be off the center axis of the outer circumferential surface. Moreover, parting lines which are positioning structures are provided on the cap and the housing, respectively.

4 Claims, 11 Drawing Sheets

(56) References Cited

U.S. PATENT DOCUMENTS

| | | | |
|---|---|---|---|
| 5,330,425 A | 7/1994 | Utterberg | |
| 5,578,070 A | 11/1996 | Utterberg | |
| 6,451,257 B1 * | 9/2002 | Flamer | A61M 1/3627 422/44 |
| 2008/0083409 A1 * | 4/2008 | Hamaguchi | A61M 16/20 128/205.24 |
| 2012/0152118 A1 | 6/2012 | Weaver et al. | |
| 2015/0045799 A1 * | 2/2015 | Budyansky | A61B 17/1642 606/84 |

FOREIGN PATENT DOCUMENTS

| | | | | |
|---|---|---|---|---|
| EP | 3266477 A1 * | 1/2018 | | A61M 1/3627 |
| JP | H06-142192 A | 5/1994 | | |
| JP | 3105777 U | 11/2004 | | |
| JP | 3936121 B2 | 6/2007 | | |
| JP | 5931128 B2 | 6/2016 | | |

OTHER PUBLICATIONS

Nov. 18, 2021 Extended European Search Report issued in European Patent Application No. 19796774.8.

Nov. 10, 2023 Office Action issued in European Application No. 19 796 774.8.

* cited by examiner

AIR TRAP CHAMBER AND EXTRACORPOREAL CIRCULATION CIRCUIT

TECHNICAL FIELD

The present invention relates to an air trap chamber and an extracorporeal circulation circuit including the same.

BACKGROUND

For instance, in hemodialysis, blood removed from a patient is sent to an extracorporeal circulation circuit. The extracorporeal circulation circuit includes an arterial side circuit to which the removed blood is supplied, a purifier (dialyzer) that purifies the blood sent from the arterial side circuit, and a venous side circuit that returns the purified blood to the patient.

At least one of the arterial side circuit and the venous side circuit is provided with an air trap chamber for capturing bubbles in blood flowing through the circuit (debubbling). As shown in Patent Documents 1 to 3, for example, the air trap chamber has a blood inlet and an air vent on an upper end, and a blood outlet at a lower end.

CITATION LIST

Patent Literature

Patent Document 1: JP 3936121 B
Patent Document 2: Japanese Patent Application No. Hei 6-142192
Patent Document 3: Registered Japanese Utility Model No. 3105777

SUMMARY

Technical Problem

Incidentally, when liquid flows in the direction opposite to that during dialysis treatment, such as during priming, backflow may occur, causing bubbles to enter the outlet of the air trap chamber from the downstream side thereof. The bubbles that have entered the air trap chamber rise in the chamber. When the rising bubbles reach the inlet, they enter the arterial side circuit located upstream from the air trap chamber and the blood purifier. In this case, in order to return the trapped bubbles to the air trap chamber, complicated additional work is performed; for example, the tube of the arterial side circuit or the blood purifier is moved downward or hit from the outside. A possible way of preventing entry of bubbles into the inlet is to form the air trap chamber so that the opening axis of the outlet and the opening axis of the inlet are not coaxial.

Here, the air trap chamber may consist of a cap, which is a member on the inlet side, and a housing, which is a member on the outlet side. In the process of assembling these two members, it is necessary to adjust the positions of the outlet and the inlet; that is, to make the opening axis of the outlet and the opening axis of the inlet be not coaxial with each other.

In particular, when the mating surfaces between the cap and the housing have a circular cross section, the cap and the housing before fixation can move relative to each other. At this time, when three axes: the central axis of the mating surfaces between the cap and the housing, the opening axis of the outlet, and the opening axis of the inlet, are located off-axis with respect to each other, the relative angle between the opening axis of the outlet and the opening axis of the inlet based on the central axis of the mating surfaces changes according to the relative angle between the cap and the housing.

For instance, in order to fix the cap and the housing together, an adhesive may be applied between the mating surfaces of the two, and the cap and the housing may be locked together and rotated relative to each other in order to smooth the adhesive on them; however, at this time, the relative angle between the opening axis of the outlet and the opening axis of the inlet may deviate from a predetermined design value.

Solution to Problem

The present invention relates to an air trap chamber. The air trap chamber includes a cap and a housing. The cap has an inlet at one end, and a first connection flange at the other end, the first connection flange having a first mating surface having a circular cross section, the inlet having an opening axis that is off a central axis of the first mating surface. The housing has a second connection flange at one end, and an outlet at the other end, the second connection flange having a second mating surface having a circular cross section and being mateable with the first mating surface, the outlet having an opening axis that is off a central axis of the second mating surface. The cap and the housing are provided with an alignment structure.

According to the present invention, with the alignment structure of the cap and the housing, the relative angle between the opening axis of the outlet and the opening axis of the inlet can be adjusted to a predetermined design value.

In the present invention, as the alignment structure, at least one of a parting line, a protrusion, a recessed groove, and an alignment mark is formed on the cap, and at least one of the parting line, the protrusion, the recessed groove, and the alignment mark is formed on the housing.

The present invention relates to an extracorporeal circulation circuit. The circuit circulates removed blood. This extracorporeal circulation circuit has a flow path to which the air trap chamber of the aforementioned invention is coupled.

Advantageous Effects of Invention

According to the present invention, the relative angle between the opening axis of the outlet and the opening axis of the inlet can be adjusted to a predetermined design value.

DESCRIPTION OF EMBODIMENTS

Figure 1:
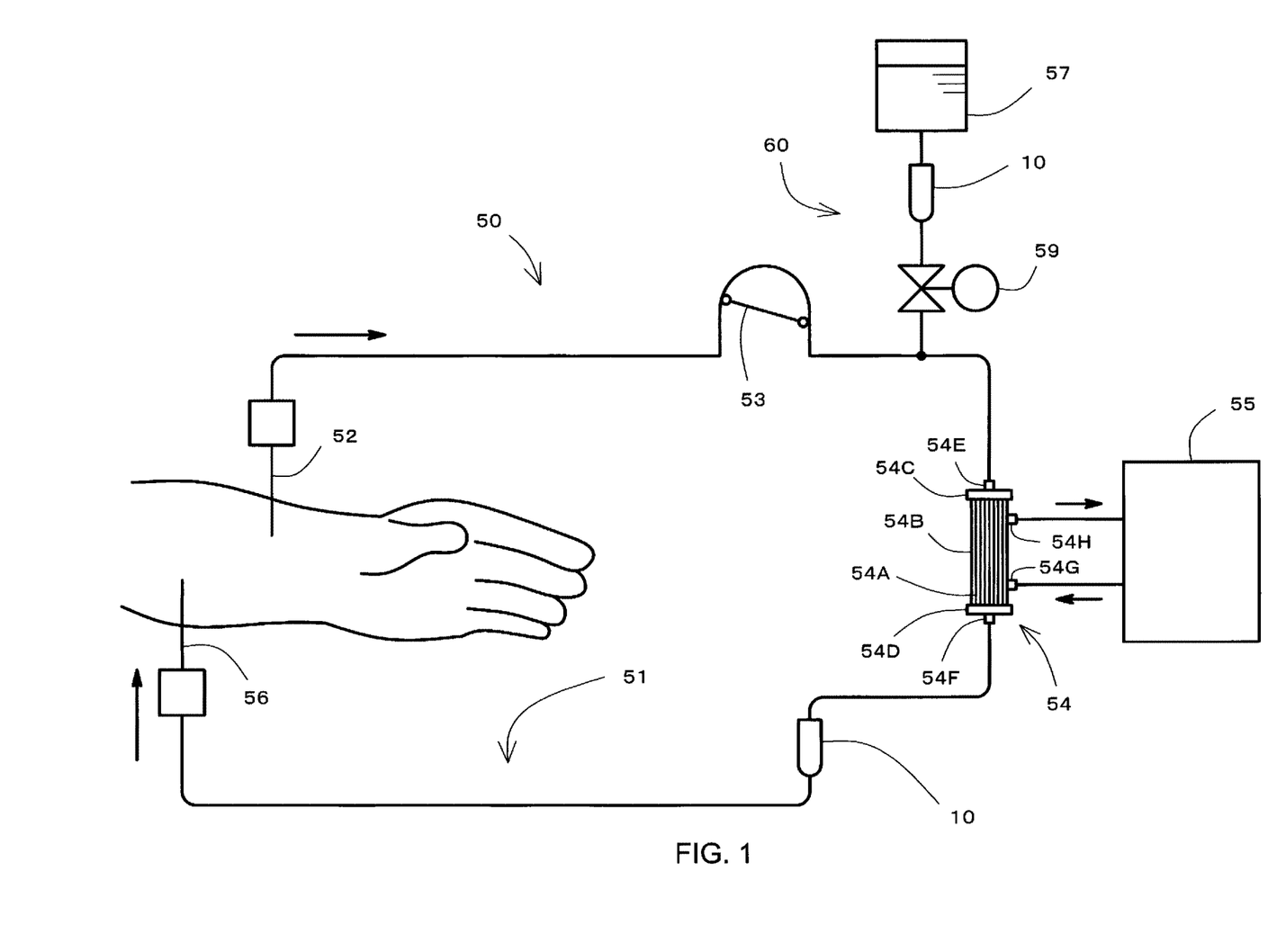
FIG. 1 is a diagram illustrating an extracorporeal circulation circuit using an air trap chamber according to an embodiment of the invention.

FIG. 1 illustrates an extracorporeal circulation circuit to which an air trap chamber 10 according to an embodiment of the invention is coupled. The extracorporeal circulation circuit is a circuit used for hemodialysis, for example, and includes an arterial side circuit 50, a blood purifier 54, a dialyzer 55, a venous side circuit 51, and a replacement liquid line 60. Note that the air trap chamber 10 according to this embodiment is coupled, but not necessarily, to the extracorporeal circulation circuit used for dialysis treatment. For instance, the air trap chamber 10 according to this embodiment may be coupled to an extracorporeal circulation circuit that circulates blood removed from a patient and can perform purification treatment. For instance, the air trap chamber 10 according to the embodiment may be coupled to an extracorporeal circulation circuit used in acetate free biofiltration (AFBF), continuous slow hemofiltration therapy, hemadsorption therapy, selective blood cell depletion therapy, simple plasma exchange therapy, double membrane filtration plasma exchange therapy, plasma adsorption therapy, or the like. The air trap chamber 10 according to this embodiment can be provided in the arterial side circuit 50, the venous side circuit 51, and the replacement liquid line 60, which will be described later, of the extracorporeal circulation circuit. In addition, the air trap chamber 10 according to the embodiment can be coupled to a path where thrombosis may occur; that is, an extracorporeal circulation circuit path in which blood or blood components flow. In addition, the air trap chamber 10 according to the embodiment can be coupled to extracorporeal circulation circuit paths in which blood or blood components flow, extracorporeal circulation circuit paths in which saline solution flows, and extracorporeal circulation circuit paths including these.

The arterial side circuit 50 is supplied with blood removed from the patient's body. The arterial side circuit 50 includes an arterial side puncture needle 52 and a roller pump 53 from the upstream side. The arterial side puncture needle 52 is introduced into a blood vessel of the patient and blood is sent to the tube of the arterial side circuit 50 (blood removal).

The roller pump 53 transports the blood in the tube to the blood purifier 54 by externally squeezing the tube. For instance, since the circuit may be filled with a priming liquid from the venous side circuit during priming, the roller pump 53 may be capable of rotating in the forward and reverse directions.

The air trap chamber 10 according to this embodiment may be coupled between the arterial side puncture needle 52 and the roller pump 53 and between the roller pump 53 and the blood purifier 54. The configuration and function of the air trap chamber 10 will be described later. It should be noted that the air trap chamber 10 in the venous side circuit 51 is indispensable for making sure to debubble the blood to be returned, whereas these air trap chambers 10 provided in the arterial side circuit 50 are optional.

The replacement liquid line 60 is provided between the roller pump 53 and the blood purifier 54 in the arterial side circuit 50. The replacement liquid line 60 is provided with a replacement liquid bag 57 and a clamp 59. The air trap chamber 10 is provided between the replacement liquid bag 57 and the clamp 59.

The replacement liquid bag 57 contains saline solution as a replacement liquid. For instance, during priming of the extracorporeal circulation circuit, the clamp 59 is opened and the saline solution is supplied from the replacement liquid bag 57 to the extracorporeal circulation circuit. Bubbles in the circuit are removed by filling the circuit with saline solution. Upon completion of the priming, the clamp 59 is closed.

Upon completion of the dialysis treatment, the clamp 59 is opened again to return the blood from the circuit to the patient's body, filling the circuit with saline solution from the replacement liquid bag 57. In other words, the blood in the circuit is replaced with saline solution.

The blood purifier 54 purifies the blood sent from the arterial side circuit 50. The blood purifier 54 is a so-called dialyzer, and the dialysate and blood are exchanged through a hollow fiber membrane 54A, for example. In the blood purifier 54, a bundle of the hollow fiber membranes 54A (hollow fiber membrane bundle) is contained in a column 54B.

The column 54B is a cylindrical container member, and has an inlet side cap 54C at one end with respect to the direction of the central axis and an outlet side cap 54D at the other end. The inlet side cap 54C is provided with a blood inlet port 54E coupled to a connector (not shown in the drawing) at the downstream end of the arterial side circuit 50. The outlet side cap 54D is provided with a blood outlet port 54F coupled to a connector (not shown in the drawing) at the upstream end of the venous side circuit 51. Blood sent from the arterial side circuit 50 flows from the blood inlet port 54E into the hollow fiber membrane 54A.

A dialysate inlet port 54G is provided in a portion of the column 54B adjacent to the outlet side cap 54D. A dialysate outlet port 54H is provided in a portion of the column 54B adjacent to the inlet side cap 54C. The dialysate is sent from the dialyzer 55 into the column 54B through the dialysate inlet port 54G. The dialysate and blood are exchanged via the hollow fiber membranes 54A, thereby purifying the blood. The dialysate after the exchange is returned to the dialyzer 55 via the dialysate outlet port 54H. The purified blood is sent to the venous side circuit 51 via the blood outlet port 54F.

In the venous side circuit 51, the purified blood is returned to the patient's body via a venous side puncture needle 56. The air trap chamber 10 is provided in the venous side circuit 51 in order to remove bubbles in the blood (debubble) when blood is returned.

Figure 2:
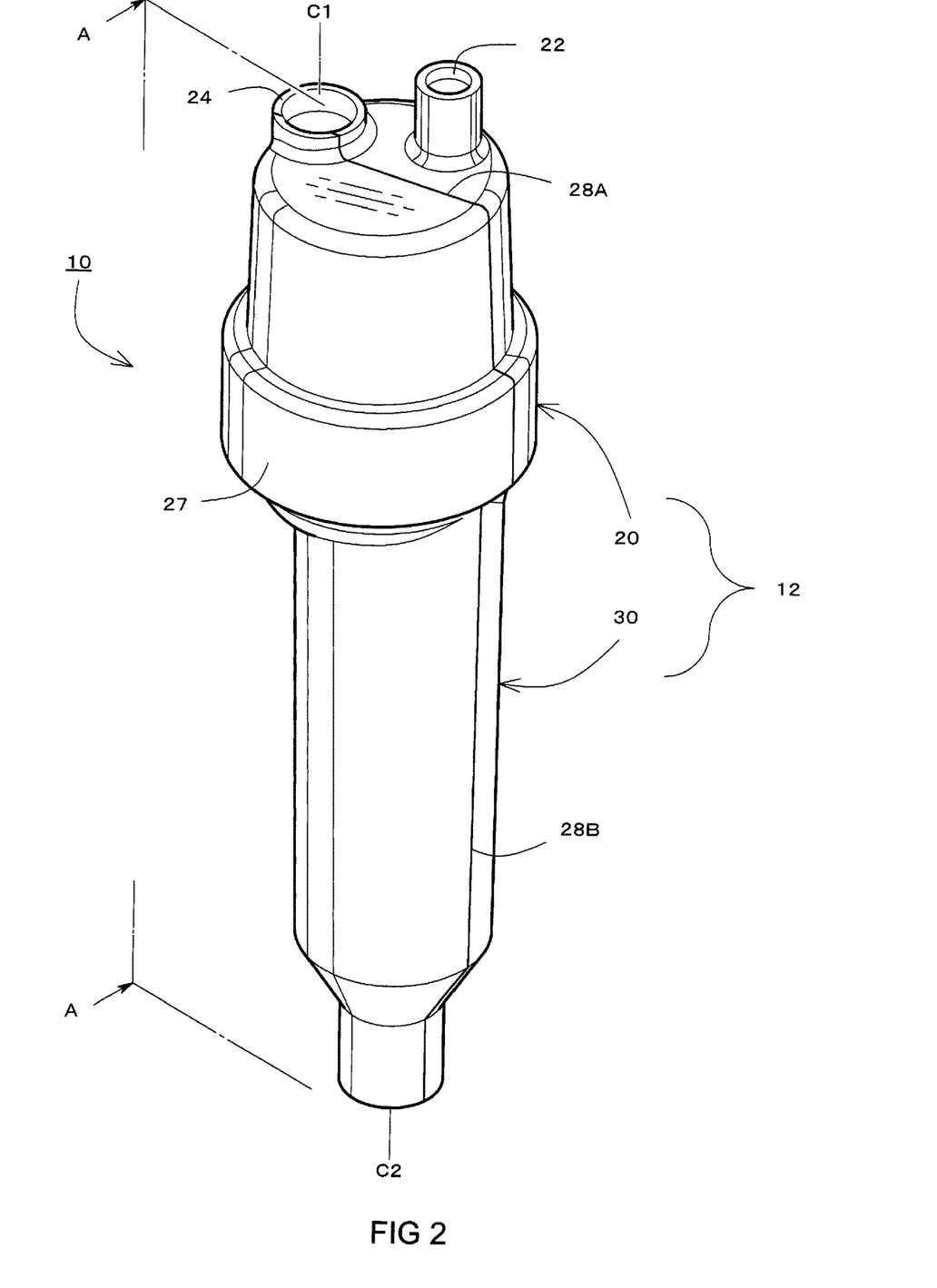
FIG. 2 is a perspective view illustrating the air trap chamber according to the embodiment.
Figure 3:
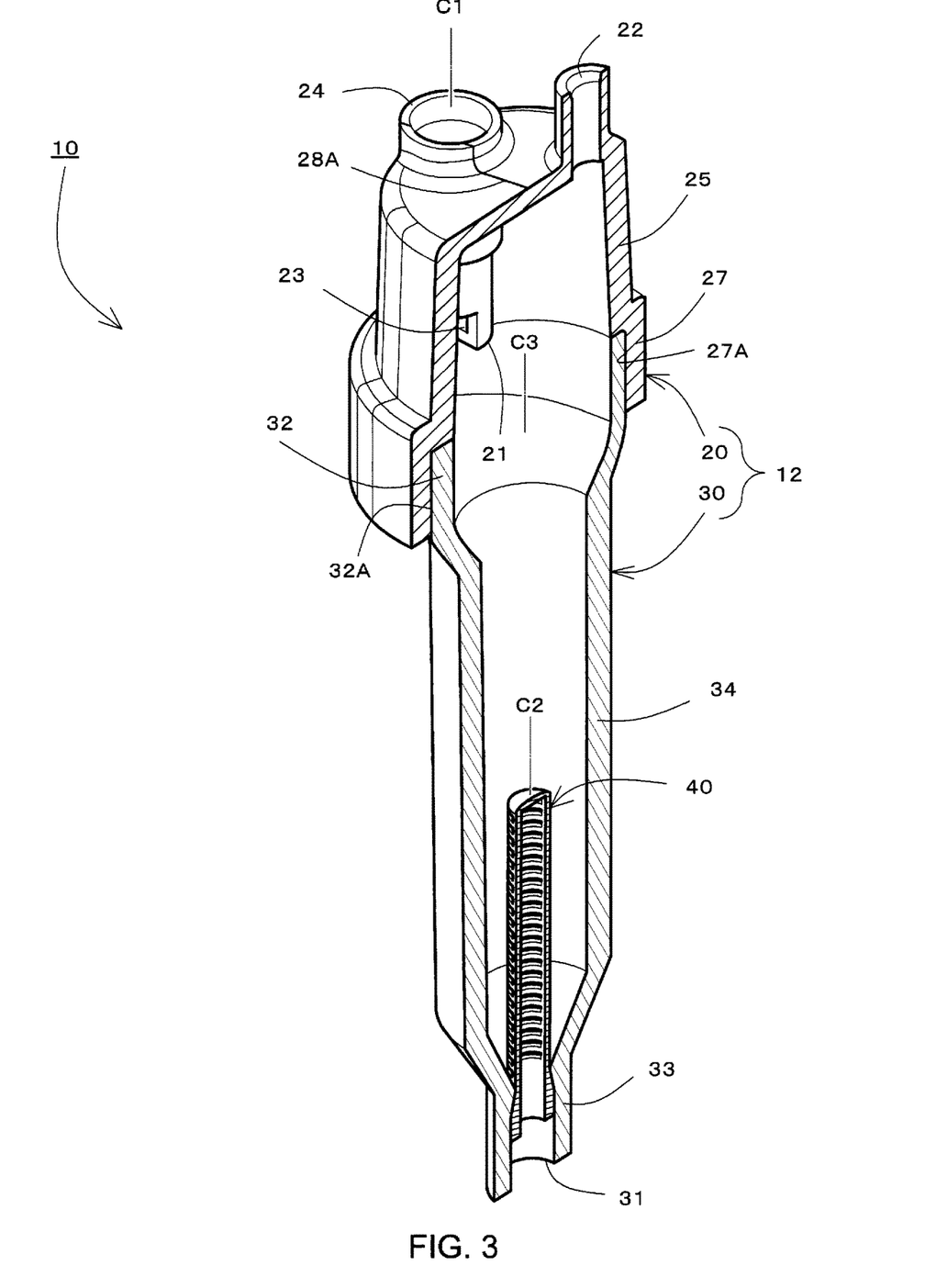
FIG. 3 is a perspective sectional view illustrating the air trap chamber according to the embodiment.

FIG. 2 illustrates the air trap chamber 10 according to the embodiment. FIG. 3 illustrates a perspective sectional view of the air trap chamber 10. The air trap chamber 10 includes a chamber body 12 and a filter 40.

During the dialysis treatment, the air trap chamber 10 is used upright so that its upper side in the drawing is the upper side and its lower side in the drawing is the lower side. Unless otherwise specified, the position and configuration of each component will be explained below with reference to the upright posture during use.

The chamber body 12 has a generally cylindrical shape, and has an inlet pipe 21 and an air vent 22 at one longitudinal end (upper end). An outlet 31 is provided at the other longitudinal end (lower end). In other words, in the chamber body 12, a liquid (for example, blood or saline solution) flows down from the inlet pipe 21 to the outlet 31.

The chamber body 12 may consist of, for example, a cap 20 and a housing 30. The cap 20 and the housing 30 are obtained by, for example, injection molding a resin. At the time of molding, a minute gap is formed at the joint between the movable side mold and the fixed side mold and resin enters it, so that linear structures called parting lines 28A and 28B are formed on the surfaces of the cap 20 and the housing 30. As will be described later, in the air trap chamber 10 according to the embodiment, the parting lines 28A and 28B are used as an alignment structure for the cap 20 and the housing 30.

Figure 4:
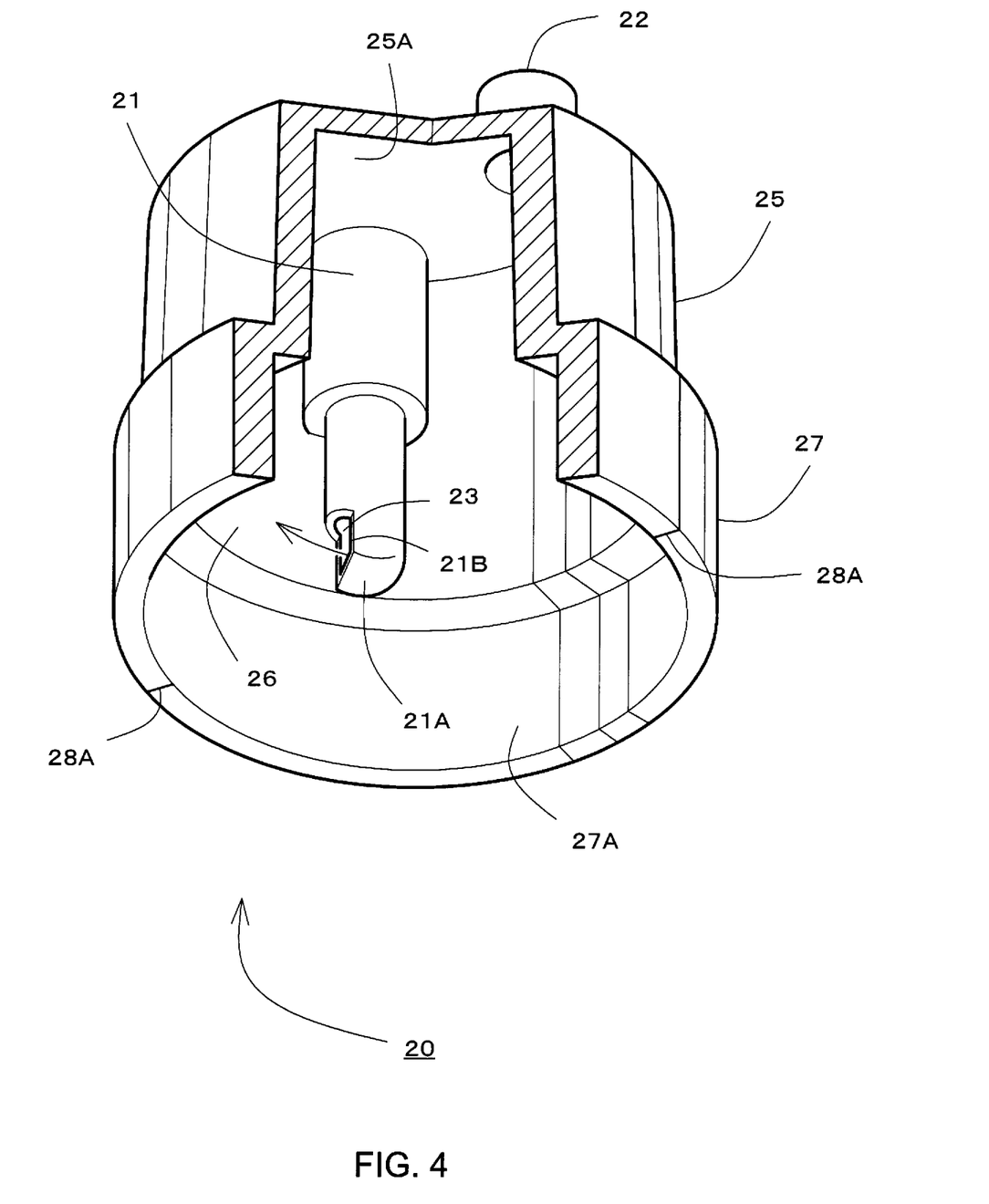
FIG. 4 is a diagram illustrating a structure of a cap of the air trap chamber according to the embodiment.

FIG. 4 illustrates a perspective sectional view of the cap 20. The cap 20 is an upper member of the chamber body 12, and is a member having a U-shaped cross section and the inlet pipe 21 and the air vent 22 at the upper end (one end). The cap 20 includes a cap body 25, a first connection flange 27, and the inlet pipe 21.

The cap body 25 is a liquid contact portion whose inner surface is to come into contact with liquid and has a cylindrical shape in which one longitudinal end (upper end) is closed with a top wall 25A. An inlet 24 (see FIG. 3) and the air vent 22 are formed in the top wall 25A. The other end (lower end) of the cap body 25 is coupled to the first connection flange 27. The first connection flange 27 is the other longitudinal end (lower end) of the cap 20.

The inlet pipe 21 is extended from the top wall 25A to the inside of the cap body 25; that is, the inside of the chamber body 12. When the air trap chamber 10 is provided in the venous side circuit 51, the inlet 24, which is bonded to the tube on the upstream side of the venous side circuit 51 with a solvent, is formed at the upper end of the inlet pipe 21. An ejection port 23, which ejects liquid into the chamber body 12, is formed at the lower end of the inlet pipe 21. As the ejection port 23 is provided below the top wall 25A in this way, bubble leak, the phenomenon in which bubbles in the chamber body 12 leak from the inlet pipe 21 to the upstream side of the venous side circuit 51, can be prevented.

In other words, for instance, when the ejection port 23 is provided at the lower surface of the top wall 25A; that is, at the same height as the air vent 22, the bubbles in the chamber may move to the ejection port 23 without going to the air vent 22, and then leak to the upstream side of the venous side circuit 51. For this reason, in the air trap chamber 10 according to the embodiment, the ejection port 23 is lowered to the inside of the chamber to prevent air bubbles from being mixed into the upstream side of the venous side circuit 51.

Figure 8:
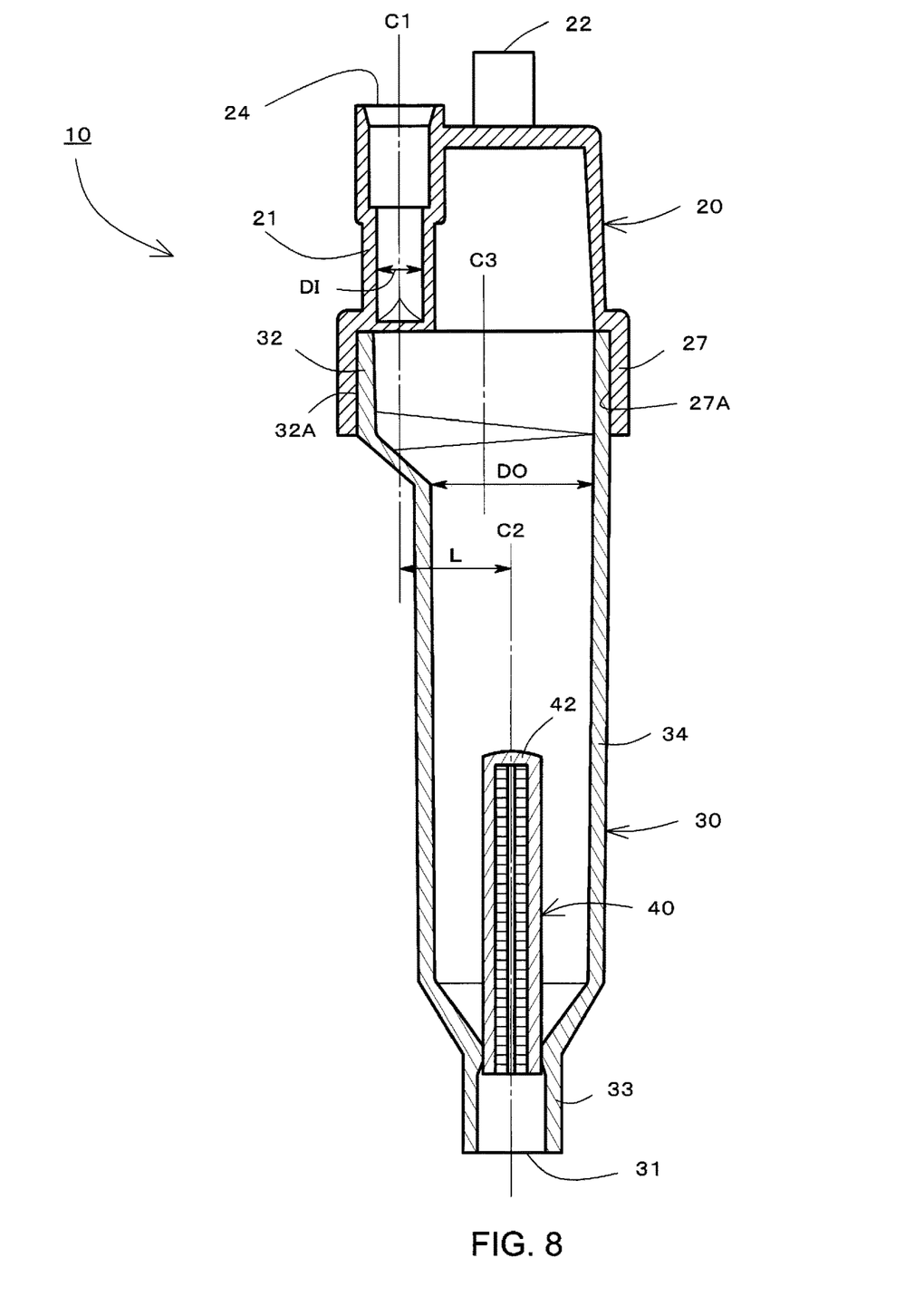
FIG. 8 is a cross-sectional view along line A-A in FIG. 2.

In addition, referring to FIG. 8, an opening axis C1 of the inlet 24 (inlet pipe 21) is provided off-axis from a central axis C3 of an inner peripheral surface 27A that is the mating surface of the first connection flange 27. With such positioning, as will be described later, when bubbles flowing back from the outlet 31 rise, the inlet 24 can be removed from the path of the rising bubbles.

The ejection port 23 of the inlet pipe 21 is provided along an inner peripheral surface 26 of the cap body 25, and has an opening facing in the circumferential direction of the inner peripheral surface 26. For instance, a lower wall 21A is formed at the lower end of the inlet pipe 21 and its side wall is cut out, forming the ejection port 23. For instance, the ejection port 23 is extended parallel to the tangential direction of the inner peripheral surface 26. A cut surface 21B of the ejection port 23 is formed so as to be parallel to the radial direction of the inner peripheral surface 26.

Since the ejection port 23 is provided in the inner peripheral surface 26 of the cap body 25 and extended in the circumferential direction, the flow of the liquid (for example, blood or saline solution) flowing out from the ejection port 23 becomes a swirl flow along the inner peripheral surface 26. Since the liquid flow in the air trap chamber 10 becomes a swirl flow, retention of the liquid in the air trap chamber 10 is suppressed as compared with the case where a specific flow is not formed.

Figure 5:
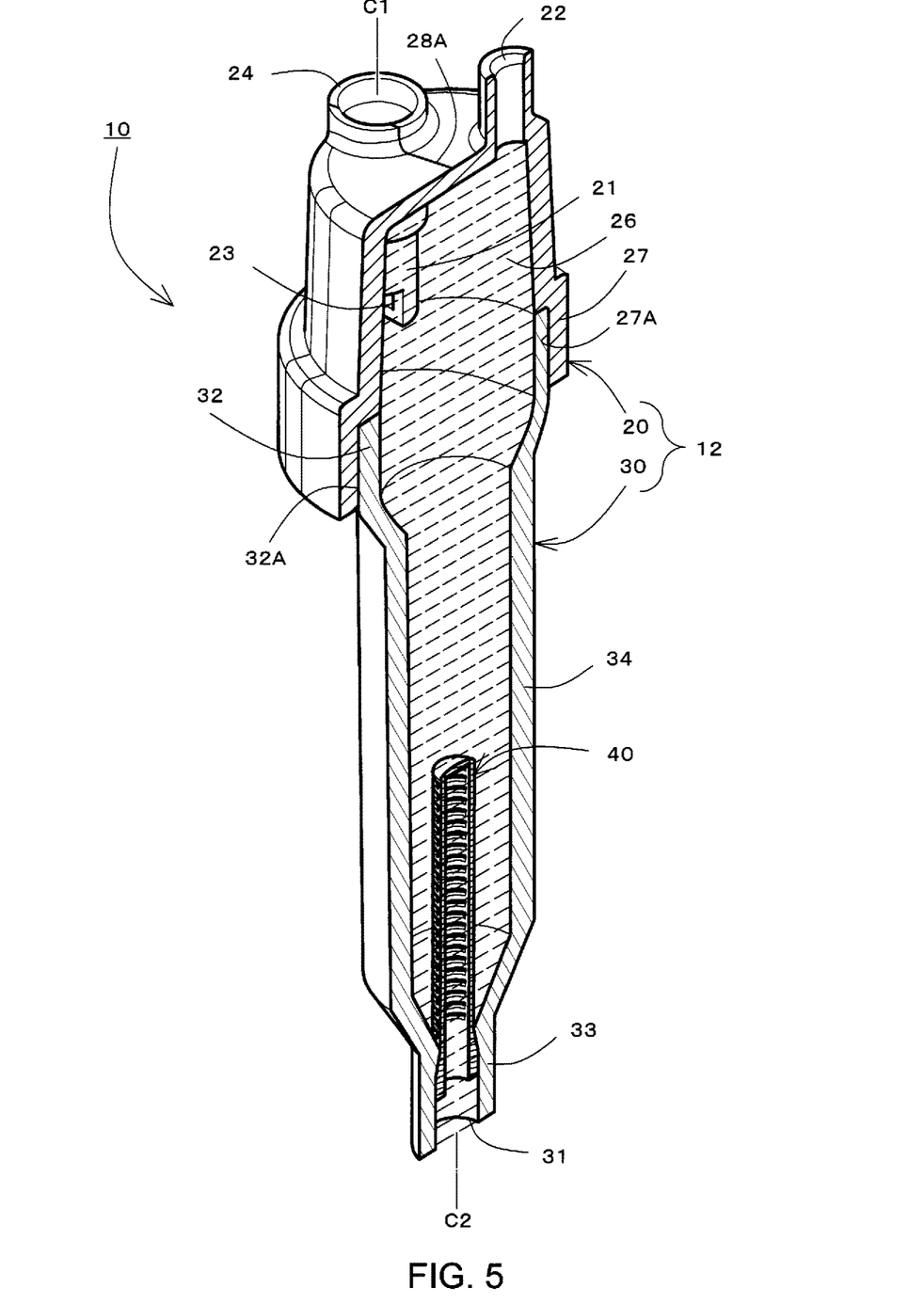
FIG. 5 is a perspective sectional view illustrating the air trap chamber according to the embodiment during use.

FIG. 5 illustrates the state of the air trap chamber 10 during dialysis treatment. The air trap chamber 10 may be a so-called airless chamber in which almost the entire internal space of the chamber body 12 is filled with a liquid (for example, blood or saline solution) as shown by the hatching in the drawing.

Figure 6:
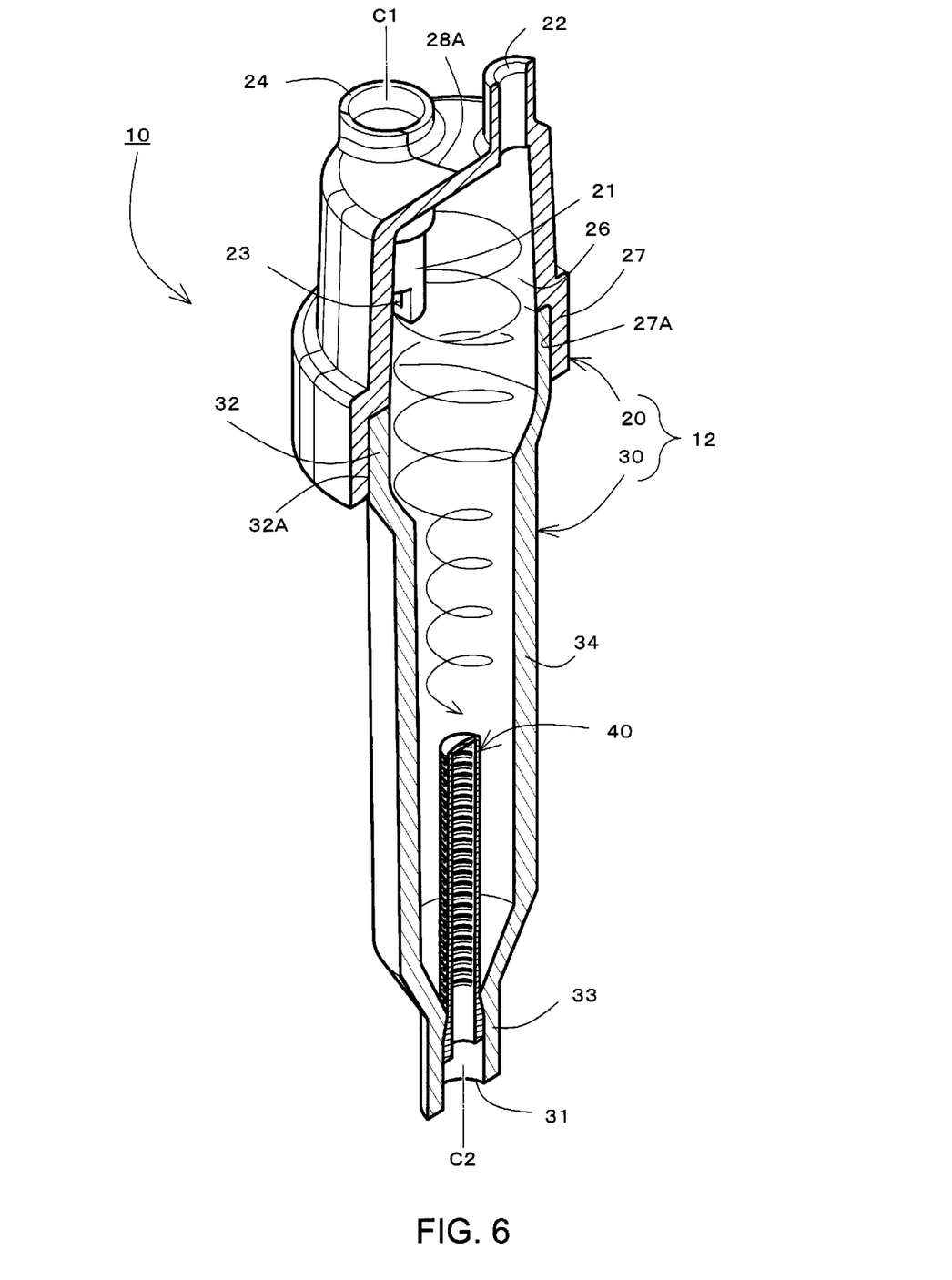
FIG. 6 is a diagram illustrating the flow in the air trap chamber according to the embodiment.

With the chamber body 12 filled with the liquid as described above, the liquid further flows in through the ejection port 23. Since the ejection port 23 is provided on the inner peripheral surface 26 of the cap 20 and extended in the circumferential direction as described above, the flow of the liquid flowing from the ejection port 23 becomes a swirl flow along the inner peripheral surface 26 as illustrated in FIG. 6. The liquid in the chamber body 12 is sent from the outlet 31 to the venous side circuit 51 via the filter 40 while maintaining the state of the swirl flow.

Referring back to FIG. 3, the first connection flange 27 is coupled to the lower end of the cap body 25. The first connection flange 27 is, for example, a cylindrical member coaxial with the cap body 25 and has an inner diameter made larger (expanded) than the inner diameter of the cap body 25. As will be described later, the inner peripheral surface 27A of the first connection flange 27 becomes a first mating surface (having a circular cross section) to be mated with an outer peripheral surface 32A (second mating surface) of a second connection flange 32 of the housing 30.

The inner peripheral surface 27A, which is the first mating surface, may be a smooth surface without protrusions, threads, or the like. As will be described later, when the cap 20 and the housing 30 are assembled together, the inner peripheral surface 27A of the cap 20 and the outer peripheral surface 32A of the housing 30 are slid on each other. The inner peripheral surface 27A is preferably a smooth surface so that this sliding can be done smoothly. The inner peripheral surface 27A may have a circular cross section. To be specific, the cross-sectional shape is preferably a perfect circular shape without distortion, but may be slightly elliptical so long as it does not hinder the aforementioned sliding; that is, so long as it is recognized as a generally circular cross-section.

Figure 7:
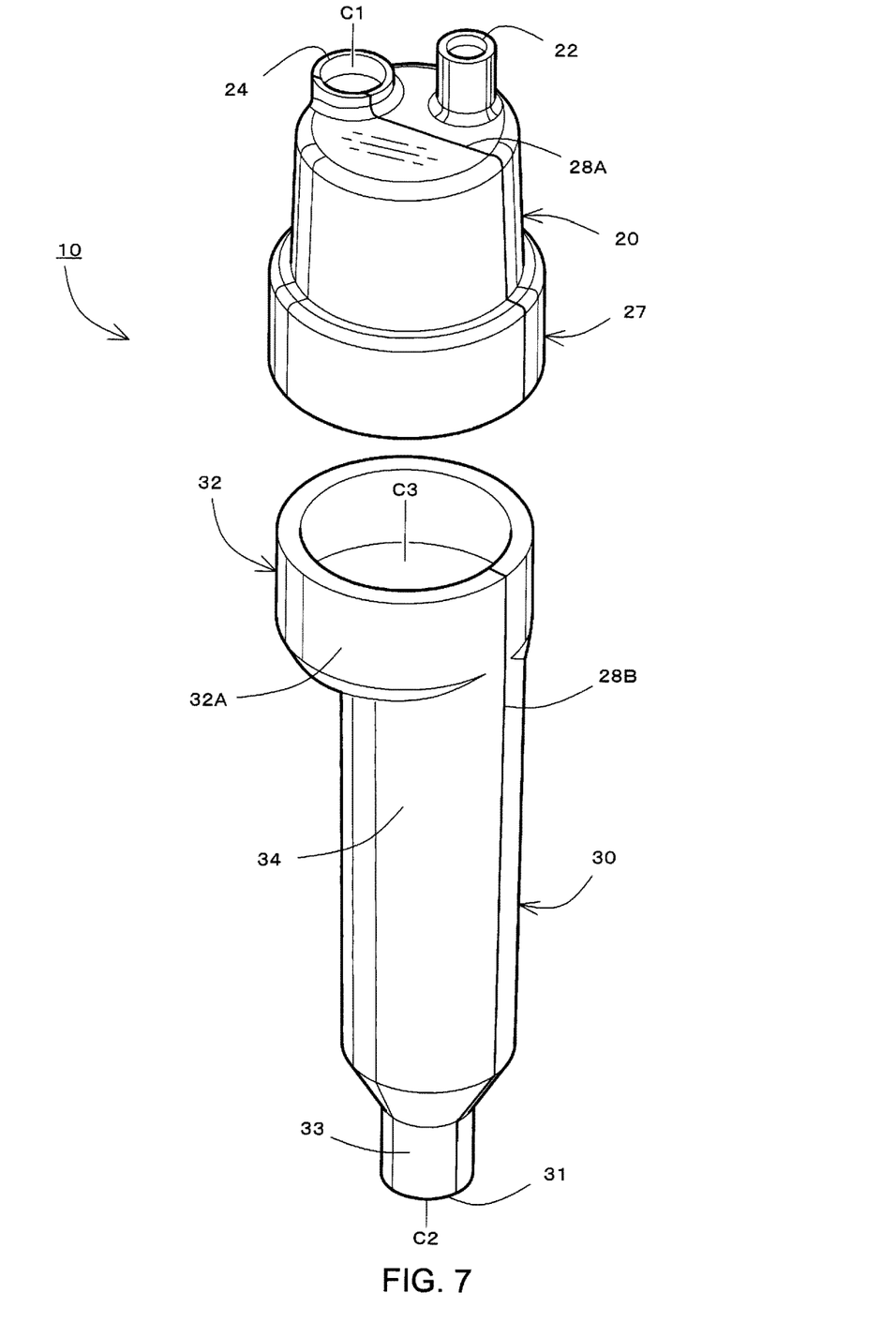
FIG. 7 is a perspective exploded view illustrating an example in which the air trap chamber according to the embodiment is disassembled into a cap and a housing.

As shown in FIGS. 3, 7, and 8, the housing 30 is a substantially cylindrical member having the second connection flange 32 at the upper end (one end) and an outlet pipe 33 at the lower end (the other end). The lower end of the outlet pipe 33 is the outlet 31. The outlet 31 is coupled, with a solvent adhesive or the like, to a tube on the upstream side of the venous side circuit 51, and passes the liquid (for example, blood or saline solution) in the air trap chamber 10 to the venous side circuit 51. A cylindrical housing body 34 is provided between the second connection flange 32 and the outlet pipe 33.

The housing 30 is configured such that the inner diameter becomes smaller from the top to the bottom; that is, in the order of the second connection flange 32, the housing body 34, and then the outlet pipe 33. With reference to FIG. 8, the second connection flange 32 and the outlet 31 are formed so that the central axis C3 of the second connection flange 32 is off an opening axis C2 of the outlet 31 (the central axis of the housing body 34). Hence, as illustrated in FIG. 7, the second connection flange 32 is coupled eccentric to the housing body 34.

The housing body 34 and the outlet pipe 33 are coaxially formed. Consequently, the opening axis C2 of the outlet 31 is off the central axis C3 of the second connection flange 32. As described above, the opening axis C1 of the inlet 24 of the cap 20 is off the central axis C3 of the first connection flange 27. In addition, the opening axis C2 of the outlet 31 is off the central axis C3 of the second connection flange 32. As shown in the drawing, the opening axes C1 and C2 and the central axis C3 are parallel with each other. With such positioning, the opening axis C1 of the inlet 24 can be located off the opening axis C2 of the outlet 31. As a result, when bubbles flowing back from the outlet 31 rise, entrance of the bubbles to the inlet 24 is suppressed.

For instance, when the inner diameter DO of the housing body 34 and the inner diameter DI of the inlet pipe 21 are used, the distance L between the opening axis C1 of the inlet pipe 21 and the opening axis C2 of the outlet 31 is preferably L>(DI+DO)/2. When the housing body 34 has a tapered shape in which the inner diameter decreases toward the lower end, the maximum inner diameter of the tapered shape may be the inner diameter DO.

The outer peripheral surface 32A of the second connection flange 32 becomes a second mating surface to be mated with the inner peripheral surface 27A (first mating surface) of the first connection flange 27 of the cap 20. Like the inner peripheral surface 27A of the first connection flange 27, the outer peripheral surface 32A of the second connection flange 32 may be a smooth surface without protrusions, threads, or the like. The cross-sectional shape of the outer peripheral surface 32A is preferably a perfect circular shape without distortion, but may be slightly elliptical so long as it does not hinder the aforementioned sliding; that is, so long as it is recognized as a generally circular cross-section.

Referring to FIG. 7, parting lines 28A and 28B are formed on the cap 20 and the housing 30, respectively. The parting lines 28A and 28B are used as an alignment structure for assembling of the cap 20 and the housing 30.

Figure 9:
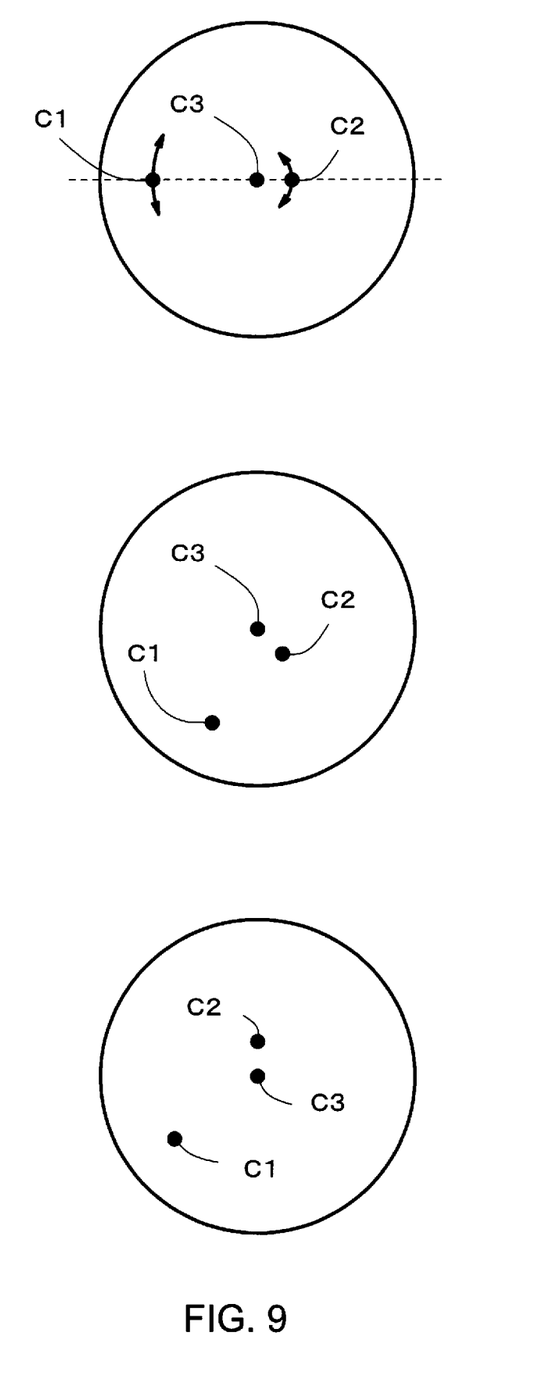
FIG. 9 is a diagram illustrating relative displacement among the central axis of the mating surfaces, the opening axis of the inlet, and the opening axis of the outlet.

For instance, the parting lines 28A and 28B are formed so that they coincide with each other when the opening axis C1 of the inlet 24, the opening axis C2 of the outlet 31, and the central axis C3 of the first connection flange 27 are linearly arranged as shown in the upper part of FIG. 9. For example, the parting line 28A is formed on the cap 20 and the parting line 28B is formed on the housing 30 during injection molding by adjusting the shapes and positions of the movable mold and the fixed mold.

<Assembly of Air Trap Chamber>

The assembly of the air trap chamber 10 according to this embodiment will be described below. First, the filter 40 is assembled to the housing body 34. Referring to FIG. 8, the filter 40 is inserted into the chamber from the outlet 31 so that a ceiling section 42 of the filter 40 is inserted first. A tube (not shown in the drawing) coated with a solvent (adhesive) is pushed into a space between the inner peripheral surface of the outlet pipe 33 and the outer peripheral surface of the bottom of the filter 40, thereby positioning the filter 40. At the time of this positioning, the tube is bonded to the inner peripheral surface of the outlet pipe 33 with the solvent. In this way, the tube seals the space between the housing 30 and the filter 40.

Next, the cap 20 is attached to the housing 30. An adhesive (solvent) is applied to at least one of the inner peripheral surface 27A of the first connection flange 27 of the cap 20 and the outer peripheral surface 32A of the second connection flange 32 of the housing 30, and the second connection flange 32 is inserted into the first connection flange 27.

The cap 20 and housing 30 are rotated relative to each other to smooth the adhesive, that is, to spread the adhesive along the shapes of the inner peripheral surface 27A of the first connection flange 27 and the outer peripheral surface 32A of the second connection flange 32. At this time, the cap 20 and the housing 30 are rotated relative to each other about the central axis C3 of the first connection flange 27 and the second connection flange 32.

During this relative rotation, the opening axis C1 of the inlet 24 and the opening axis C2 of the outlet 31 are relatively displaced. For instance, as illustrated in FIG. 9, the opening axis C1 and the opening axis C2 at different distances from the central axis C3 are rotated relative to each other about the central axis C3 of the first and second connection flanges 27 and 32. For instance, the cap 20 and the housing 30 are arranged linearly so that the opening axis C1 and the opening axis C2 are most distant from each other as illustrated in the upper part of FIG. 9, or arranged zigzag so that the opening axis C1 and the opening axis C2 are close to each other as illustrated in the middle part and the lower part of FIG. 9.

After the cap 20 and the housing 30 are rotated relative to each other to smooth the adhesive, the parting line 28A of the cap 20 and the parting line 28B of the housing 30 illustrated in FIG. 7 are aligned into the linear arrangement in the upper part of FIG. 9. For instance, the cap 20 and the housing 30 are positionally aligned so that the parting lines 28A and 28B are aligned in a line. The adhesive is then cured so that the cap 20 and the housing 30 are fixed together. This makes it possible to adjust the relative angle between the opening axis C2 of the outlet 31 and the opening axis C1 of the inlet 24 to a predetermined design value.

In the aforementioned embodiment, the first mating surface of the cap 20 is used as the inner peripheral surface 27A of the first connection flange 27, and the second mating surface of the housing 30 is used as the outer peripheral surface 32A of the second connection flange 32; however, this is not necessarily the case. In short, the connection flanges should radially face each other as their positional relationship and, with the diameter of the first connection flange 27 smaller than that of the second connection flange 32, the outer peripheral surface of the first connection flange 27 may be used as the first mating surface and the inner peripheral surface of the second connection flange 32 may be used as the second mating surface.

<Another Example of Alignment Structure>

Figure 10:
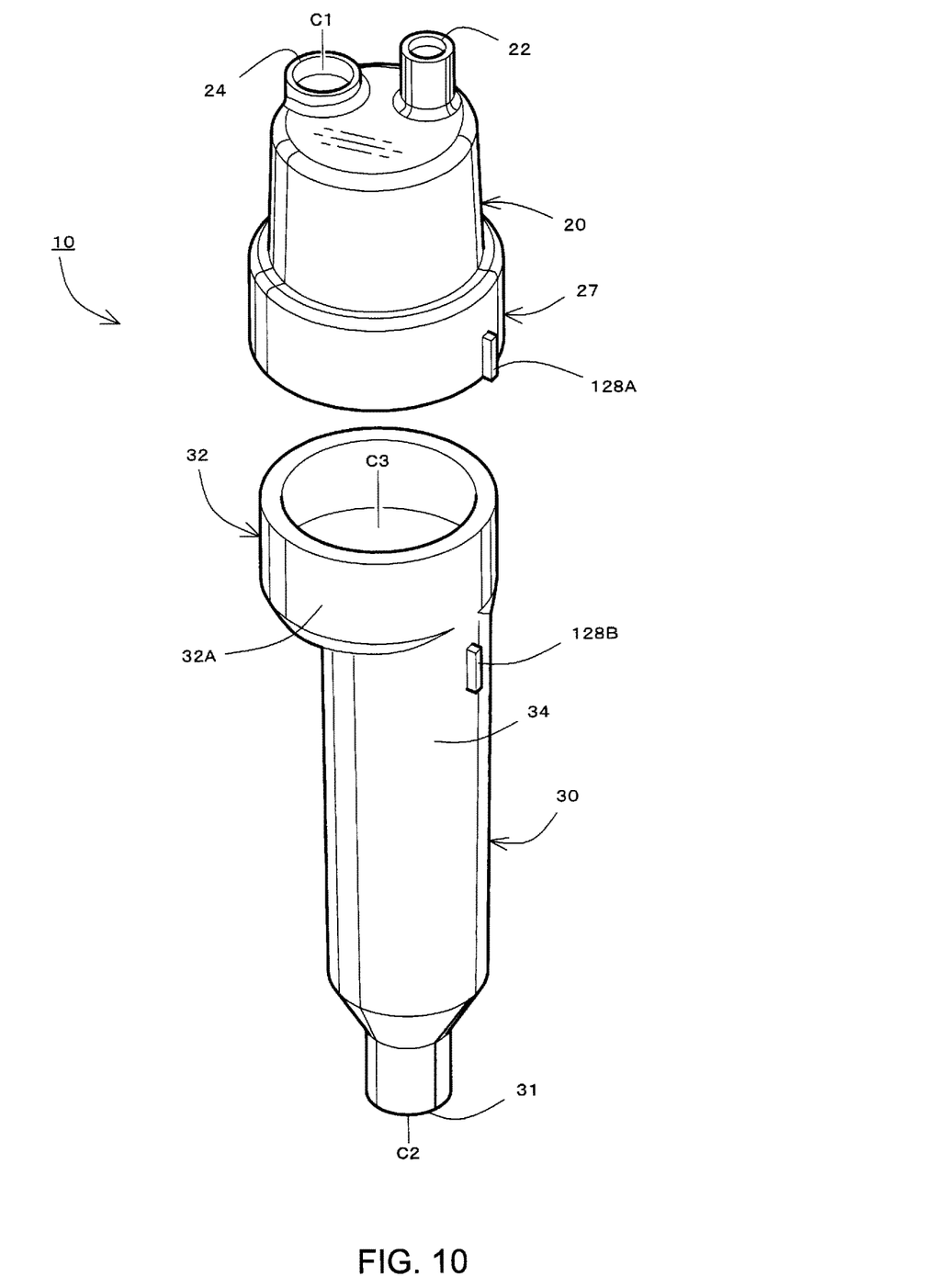
FIG. 10 is a perspective exploded view illustrating an air trap chamber according to another example of the embodiment.

FIG. 10 illustrates another example of the air trap chamber 10 according to the embodiment. In this example, instead of the parting lines 28A and 28B, a rib 128A, which is a protrusion, is provided on the outer peripheral surface of the first connection flange 27, and a rib 128B is also provided on the outer peripheral surface of the housing body 34. The upper end of the rib 128B of the housing body 34 is, for example, provided at the lower end of the second connection flange.

In assembling the air trap chamber 10, the linear arrangement in the upper part of FIG. 9 can be obtained by aligning the positions of the ribs 128A and 128B; that is, aligning the relative positions of the cap 20 and the housing 30 so that they are aligned in a line. In other words, the relative angle between the opening axis C2 of the outlet 31 and the opening axis C1 of the inlet 24 can be adjusted to a predetermined design value.

In this way, use of protrusions, the ribs 128A and 128B, as an alignment structure makes it possible to visually check alignment, or check alignment by probing; i.e., check whether the positions are aligned by touching.

Considering that besides the visual check of the alignment, the check by probing can be achieved, a recessed groove that is depressed radially inward may be formed on the outer peripheral surface of the first connection flange 27 instead of the rib 128A, and another recessed groove may be formed on the outer peripheral surface of the housing body 34 instead of the rib 128B.

<Still Another Example of Alignment Structure>

Figure 11:
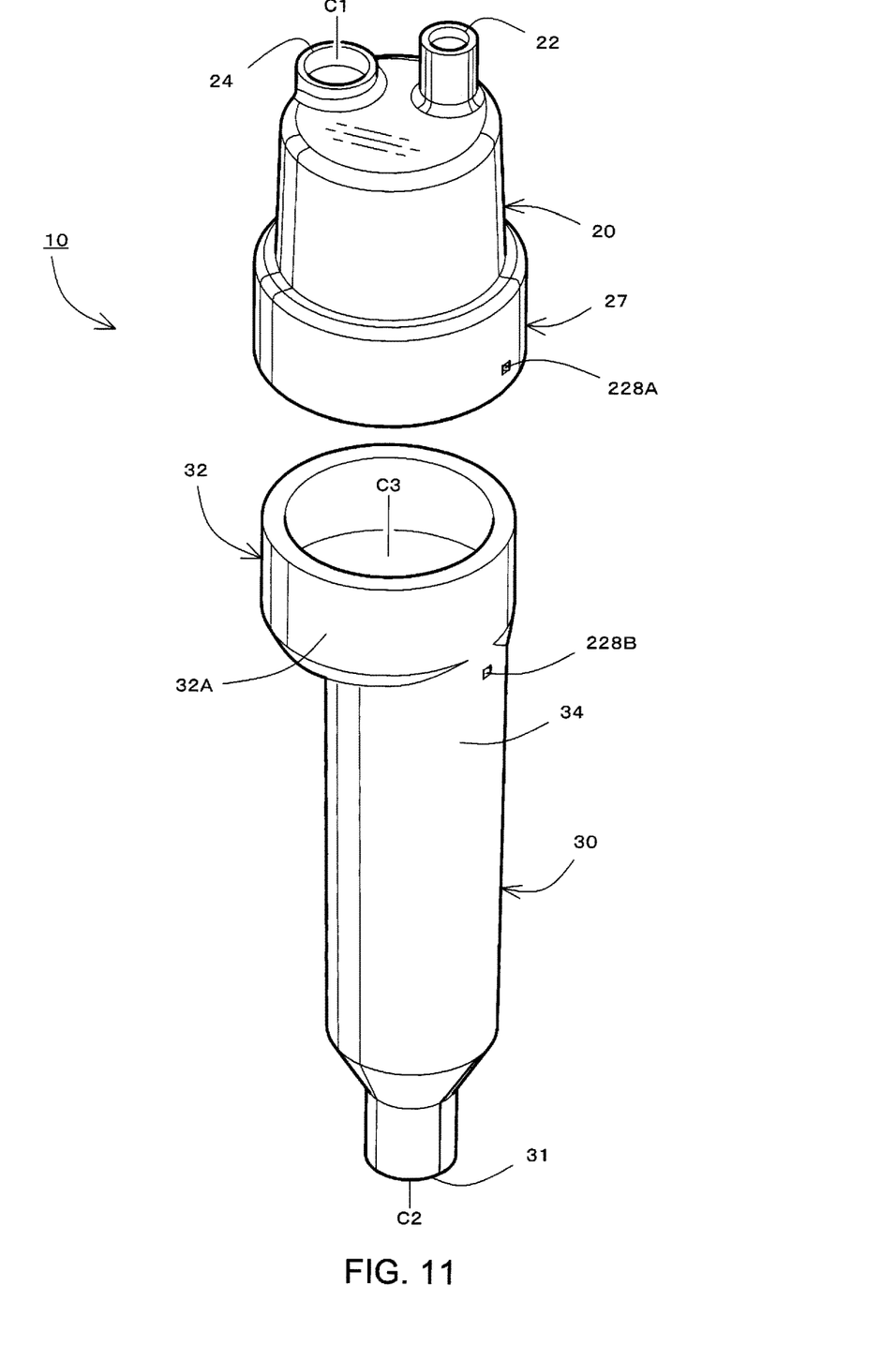
FIG. 11 is a perspective exploded view illustrating an air trap chamber according to still another example of the embodiment.

FIG. 11 illustrates still another example of the air trap chamber 10 according to this embodiment. In this example, instead of the parting lines 28A and 28B, an alignment mark 228A is printed on the outer peripheral surface of the first connection flange 27, and an alignment mark 228B is also printed on the outer peripheral surface of the housing body 34. The upper end of the alignment mark 228B of the housing body 34 is, for example, provided at the lower end of the second connection flange 32.

In assembling the air trap chamber 10, the linear arrangement in the upper part of FIG. 9 can be obtained by aligning the positions of the alignment marks 228A and 228B; that is, aligning the relative positions of the cap 20 and the housing 30 so that they are aligned in a line. In other words, the relative angle between the opening axis C2 of the outlet 31 and the opening axis C1 of the inlet 24 can be adjusted to a predetermined design value.

Printing the alignment marks 228A and 228B on the cap 20 and the housing 30 in this way ensures the alignment accuracy at the resolution level in the printing. For example, since an inkjet printer has a resolution of about 1000 Dot Per Ink (DPI), theoretically, alignment on the order of 2.54 cm×$10^{-3}$ is possible.

<Yet Another Example of Alignment Structure>

In the aforementioned embodiment, the same type of alignment structure (parting lines 28A and 28B, ribs 128A and 128B (protrusions), recessed grooves, and alignment marks 228A and 228B) is formed on the outer peripheral surface of the first connection flange 27 and the outer peripheral surface of the housing body 34; however, this is not necessarily the case. In short, since at least alignment of the cap 20 and the housing 30 is necessary, at least one of the parting line 28A, the rib 128A, the recessed groove, and the alignment mark 228A should be formed on the cap, and at least one of the parting line 28B, the rib 128B, the recessed groove, and the alignment mark 228B should be formed on the housing 30.

REFERENCE SIGNS LIST

10 Air trap chamber, 12 Chamber body, 20 Cap, 21 Inlet pipe, 22 Air vent, 23 Ejection port, 24 Inlet, 25 Cap body, 27 First connection flange, 27A Inner peripheral surface of first connection flange (first mating surface), 28A, 28B Parting line (alignment structure), 30 Housing, 31 Outlet, 32 Second connection flange, 32A Outer peripheral surface of second connection flange (second mating surface), 33 Outlet pipe, 34 Housing body, 50 Arterial side circuit, 51 Venous side circuit, 54 Blood purifier, 55 Dialyzer, 128A, 128B Rib (alignment structure), 228A, 228B Alignment mark (alignment structure)

The invention claimed is:

1. An air trap chamber comprising:
   a cap having an inlet at one end, and a first connection flange at another end, the first connection flange having a first mating surface having a circular cross section, the inlet having an opening axis that is off a central axis of the first mating surface; and
   a unitary housing having a second connection flange at one end, and an outlet at another end, the second connection flange having a second mating surface having a circular cross section and being mateable with the first mating surface, the outlet having an opening axis that is off a central axis of the second mating surface, wherein:
   the outlet is configured to directly connect to an extracorporeal circulation circuit,
   the cap and the housing are provided with an alignment structure, and the cap and the housing are configured to be assembled such that the alignment structure formed on the cap is aligned with the alignment structure formed on the housing, and a relative angle between the opening axis of the inlet and the opening axis of the outlet is a predetermined design value, and
   as the alignment structure, at least one of a parting line, a protrusion, a recessed groove, and an alignment mark is formed on the cap, and at least one of the parting line, the protrusion, the recessed groove, and the alignment mark is formed on the housing.

2. The air trap chamber according to claim 1, wherein the alignment structure is formed on outer peripheral surfaces of the cap and the housing.

3. An extracorporeal circulation circuit that circulates removed blood and has a flow path to which the air trap chamber according to claim 1 is coupled.

4. The air trap chamber according to claim 1, wherein the opening axis of the inlet, the opening axis of the outlet, and the central axes of the first and second mating surfaces are linearly positionable to the relative angle by aligning the alignment structure of the cap with the alignment structure of the housing.

* * * * *